(12) United States Patent
Jones

(10) Patent No.: US 6,945,988 B1
(45) Date of Patent: Sep. 20, 2005

(54) DEVICE FOR COOLING SHOULDER JOINT AND NEARBY MUSCLES

(76) Inventor: Barbara J. Jones, 2610 Autumn Springs La., Spring, TX (US) 77373

( * ) Notice: Subject to any disclaimer, the term of this patent is extended or adjusted under 35 U.S.C. 154(b) by 0 days.

(21) Appl. No.: 10/832,855

(22) Filed: Apr. 27, 2004

(51) Int. Cl.⁷ .............................................. A61F 7/08
(52) U.S. Cl. ..................... 607/108; 607/114
(58) Field of Search ................... 607/108–112, 114; 602/19

(56) References Cited

U.S. PATENT DOCUMENTS

| | | |
|---|---|---|
| 3,889,684 A | 6/1975 | Lebold |
| 4,742,827 A | 5/1988 | Lipton |
| 4,753,240 A | 6/1988 | Sparks |
| 4,972,832 A | 11/1990 | Trapini et al. |
| 5,215,080 A | 6/1993 | Thomas et al. |
| 5,743,867 A | 4/1998 | Hickling |
| 6,024,761 A * | 2/2000 | Barone et al. .............. 607/108 |
| 6,440,159 B1 | 8/2002 | Edwards et al. |
| D473,656 S | 4/2003 | Miros et al. |

\* cited by examiner

*Primary Examiner*—Michael Peffley
*Assistant Examiner*—Aaron Roane
(74) *Attorney, Agent, or Firm*—Mary J. Gaskin

(57) ABSTRACT

A flexible overlay for providing cooling therapy to the shoulder joint and the upper arm area. The overlay has pockets for holding cooling material; additional pockets can be attached to it in order to cool chest and/or back muscles or more of the upper arm area. One end of the overlay is removably secured around the neck, and the other end is wrapped around the wearer's upper arm. The overlay is typically made from a soft fabric such as cotton, but can also be made from a disposable plastic material.

11 Claims, 3 Drawing Sheets

DEVICE FOR COOLING SHOULDER JOINT AND NEARBY MUSCLES

FIELD OF THE INVENTION

The present invention relates to using cooling materials as a therapeutic medical procedure and, more particularly, to a cryotherapeutic compress.

BACKGROUND OF THE INVENTION

Several facts are well known by therapists: that cooling reduces pain by decreasing electrical conduction velocity in nerves; that cooling reduces inflammation by decreasing cellular permeability; and that cooling limits topical swelling by causing capillary constriction.

Numerous prior art cold packs have been developed for application to parts of the human body which need cooling therapy. Some of these devices are in the form of bandages and compresses, and some have a number of cooling gel compartments. For use on limbs and joints, most have some type of anchoring straps, with complementary mating fasteners on the body of the overlay and at the ends of the straps. The shape of each device and the arrangement of straps used are selected to meet a variety of physical and anatomical conditions requiring cooling therapy. In many devices of this type, the mating fasteners are the complementary pieces of a hook and loop fastening system, such as VELCRO®. Often the devices do not provide reliable, yet comfortable, contact with the shoulder joint in order to facilitate efficient negative thermal conduction from the cooling gel or ice to the joint.

SUMMARY OF THE INVENTION

The present invention provides a local anatomical "overlay" for providing limited cooling of the shoulder joint, with optional compartments for applying cooling to chest and/or back muscles. The overlay is made of layers of flexible fabric material, with pockets containing cooling material, either ice encased in a zippered plastic bag, or a pre-formed ice pack, cold gel pack, or "instant" ice pack. The overlay is large enough to extend over the whole shoulder area, as well as the upper arm of the wearer. The main pocket for holding cooling material extends from the wearer's neck to the rounded rotator cuff area of the shoulder. A second pocket overlays the upper arm. Additional pockets can be attached to the overlay in order to cool chest and/or back muscles, or to cool an area further down the arm.

Fasteners on three sides of the overlay are used to hold it onto the wearer's shoulder and upper arm. The upper segment of the overlay is secured around the neck with straps that can be tied or fastened using a complementary hook and loop fastening system, D-rings, buttons, clasps, hook and eye combination, string ties; or a similar fastening system. The same type of fastening systems are used to wrap the lower segment of the overlay around the wearer's upper arm.

Instead of using fabric, the overlay can be made disposable by making it from a lightweight waterproof plastic material. The wearer can use string ties or straps with adhesive pull tabs to secure one end over the affected shoulder area, and adhesive pull tabs to secure the other end around the upper arm.

It is an object of the present invention to provide an overlay for effectively distributing cooling therapy to an affected shoulder and proximate areas.

Yet another object of the present invention is to provide an overlay which will be held securely onto the shoulder area, without restricting the wearer's activities.

A further object of the present invention is to provide an overlay to which can be attached additional pockets holding ice for application to chest and shoulder muscles.

Still another object of the present invention is to provide an overlay that is comfortable to wear and easy to clean.

One other object of the invention is to provide a design for a shoulder overlay which can be made of disposable materials.

BRIEF DESCRIPTION OF THE PREFERRED EMBODIMENT

Figure 1:
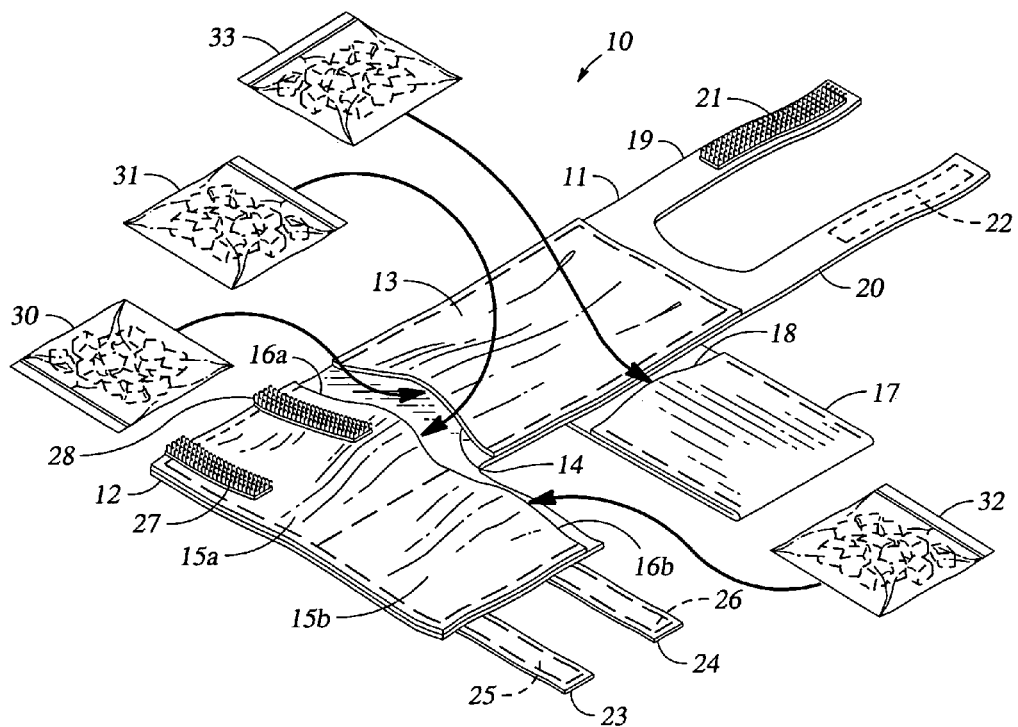
FIG. 1 is a perspective top view of the overlay of the present invention, laid flat, showing ice packs for placement in the ice pockets.
Figure 2:
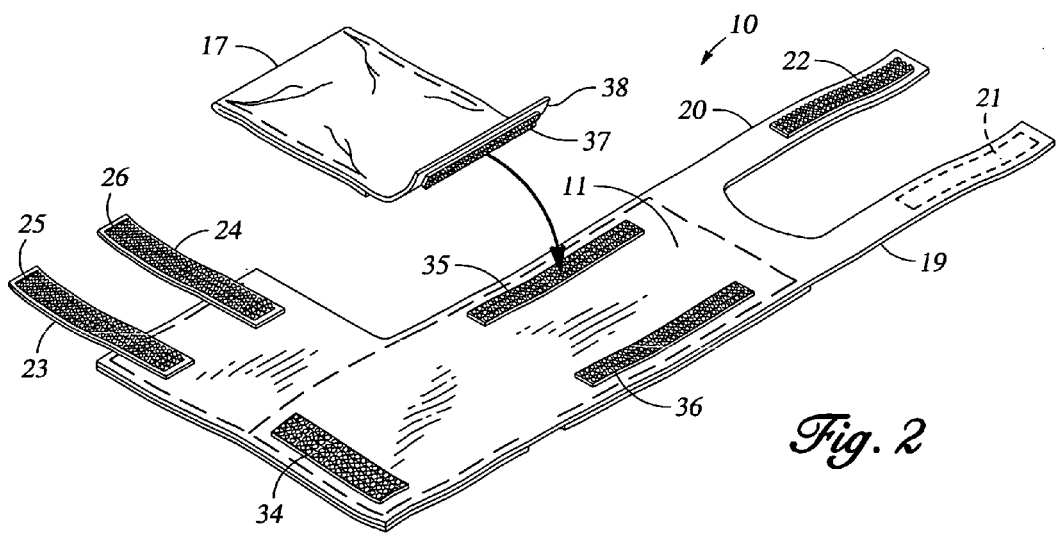
FIG. 2 is a bottom perspective view of the overlay of the present invention, laid flat, showing an optional ice pocket.

The overlay 10 of the present invention is shown laid flat in FIG. 1 and FIG. 2. The generally L-shaped overlay 10 is typically made of a soft fabric material such as cotton terrycloth. The overlay 10 can be fabricated in different sizes, depending on the size of the wearer. It generally covers the wearer's entire shoulder, continuing down the arm of the afflicted shoulder. A rectangular shoulder segment 11 is sized to extend over the wearer's shoulder area, while a rectangular upper arm segment 12, arranged perpendicularly to the shoulder segment 11, is sized to fit around the wearer's upper arm. A shoulder pocket 13 is formed by sewing three sides of a rectangular piece of material onto the shoulder segment 11, leaving an opening 14. Two upper arm pockets 15a, 15b are formed by sewing three sides of another rectangular piece of material onto the upper arm segment 12, and sewing a seam down the middle to form upper arm pockets 15a, 15b, with openings 16a, 16b. A removable pocket 17, with opening 18, can be attached to one side or the other of the shoulder segment 11 for icing chest or back muscles.

Two parallel neck straps 19, 20 extend from the shoulder segment 11. The neck straps 19, 20 will be wrapped around the wearer's neck and secured with a fastening system. Shown in FIG. 1 are complementary first strip 21 and second strip 22 of a hook and loop fastening system, such as VELCRO®, which are attached to the ends of the straps 19, 20. The neck straps 19, 20 can also be secured using D-rings, buttons, clasps, hooks and eyes, or string ties. The upper arm segment 12 is secured around the wearer's upper arm using upper arm straps 23, 24 with a fastening system. As shown in FIG. 1, a first strip 25 of VELCRO® is affixed to upper arm strap 23, which mates with the complementary second strip 27 of VELCRO®, which is affixed to the top side of the upper arm pocket 15. Another first strip 26 of VELCRO® is affixed to upper arm strip 24, which mates with another complementary second strip 28 of VELCRO®, which is also affixed to the topside of upper arm pocket 15*a*. While the drawing shows two straps, additional straps can be used, depending on the size of the wearer. Although not shown in the figures, one side of the upper arm segment can be extended to replace the need for straps 23, 24, and the VELCRO® strips 25, 27 can be attached directly onto the bottom side of the extension, in the same manner that VELCRO® strips 26, 28 are attached to the top side of the upper arm pocket 15*a*.

As shown, an ice pack 30 can be placed into shoulder pocket 13; another ice pack 31 can be placed in upper arm pockets 15*a*, and another ice pack 32 can be placed in upper arm pocket 15*b*; yet another ice pack 33 can be placed into removable pocket 17. The ice packs 30, 31, 32, 33 can be made by placing ice in zippered plastic bags or they can be preformed ice packs, cold gel packs, or "instant" ice packs. The structure of the overlay 10 provides for ideal placement of the ice packs. The placement of ice pack 30 into shoulder pocket 13 keeps the ice directly over an affected shoulder, not on the neck or upper arm. The ice pack(s) 31, 32 placed in upper arm pocket(s) 15*a*, 15*b* allow the wearer to adjust the position of the ice packs for maximum effectiveness.

FIG. 2 shows the bottom side of the overlay 10 of the present invention, laid flat. The removable pocket 17 can be fastened to the shoulder segment 11 with a two-part fastening system, such as VELCRO®. As shown, two first strips 35, 36 of VELCRO® are affixed to the underside of the shoulder segment 11, one on each side, and a complementary second strip 37 of VELCRO® is attached to a flap 38 on the removable pocket 17. The second strip 38 can be mated to either of the first strips 35, 36 in order to attach the removable pocket 17 to the overlay 10, as needed, for use in icing either a chest muscle or a back muscle. Another first strip 34 of VELCRO® is affixed to the underside of the upper arm segment 12, as shown, to which the second strip 38 can be mated in order to attach the removable pocket 17 to the overlay 10 for use in icing the elbow or lower arm.

Figure 3:
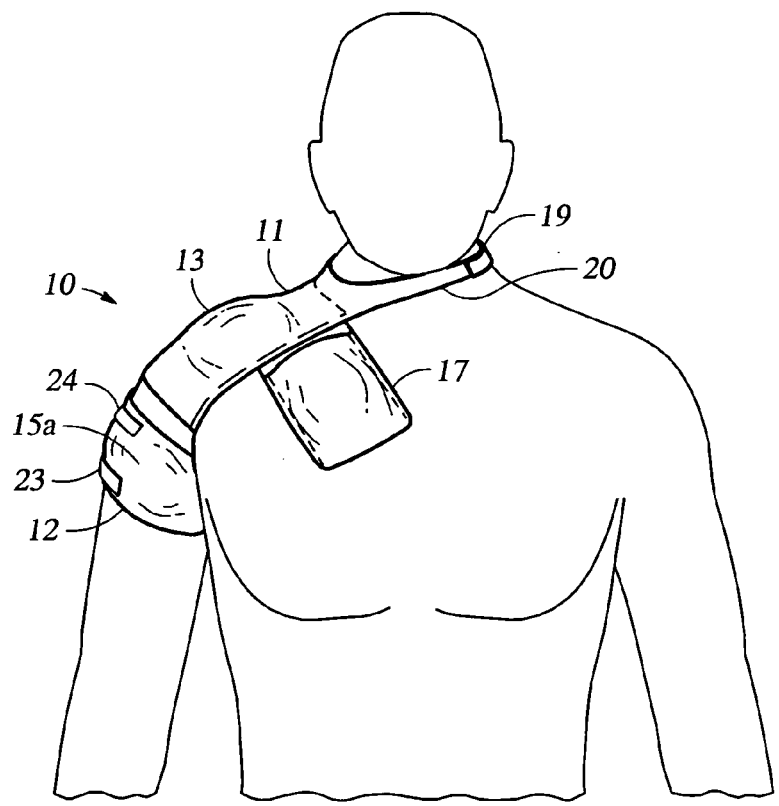
FIG. 3 is a front view of a person wearing the overlay of the present invention.

FIG. 3 shows the overlay 10 in use. The shoulder pocket 13 on the shoulder segment 11 covers the top of the shoulder area, extending from the neck to the top edge of the shoulder at the rounded rotator cuff area. The upper arm area segment 12 with upper arm pockets 15*a*, 15*b* is wrapped around the wearer's upper arm. Upper arm pocket 15*a* holds the ice pack (30) in place over the rotator cuff area. Upper arm pocket 15*b* extends around the upper arm. The overlay 10 is held on the wearer with the fastening system on neck straps 19, 20. The fastening system for upper arm straps 23, 24 holds the upper arm segment 12 onto the upper arm area. The removable pocket 17 has been attached to the shoulder segment 11 for icing a chest muscle.

Figure 4:
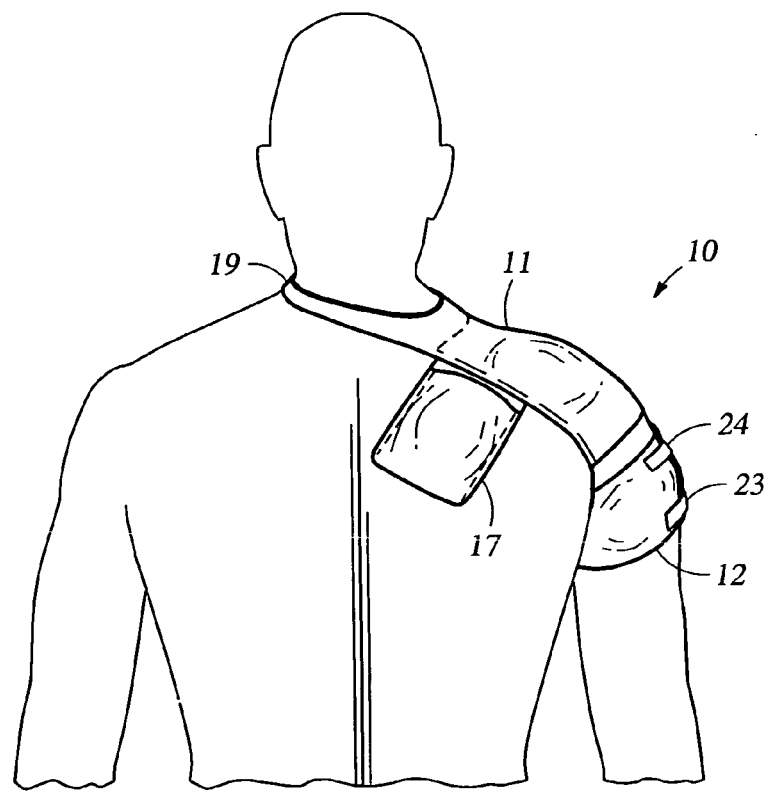
FIG. 4 is a back view of a person wearing the overlay of the present invention.

FIG. 4 shows the back of a person wearing the overlay 10. The shoulder segment 11 covers the top of the shoulder area and the upper arm segment 12 is wrapped around the wearer's upper arm. The overlay 10 is held on the wearer with the two-part fastening system on neck straps 19, (20). The fastening system for upper arm straps 23, 24 holds the upper arm segment 12 onto the upper arm area. The removable pocket 17 has been attached to the shoulder segment 11 for icing a back muscle.

Figure 5:
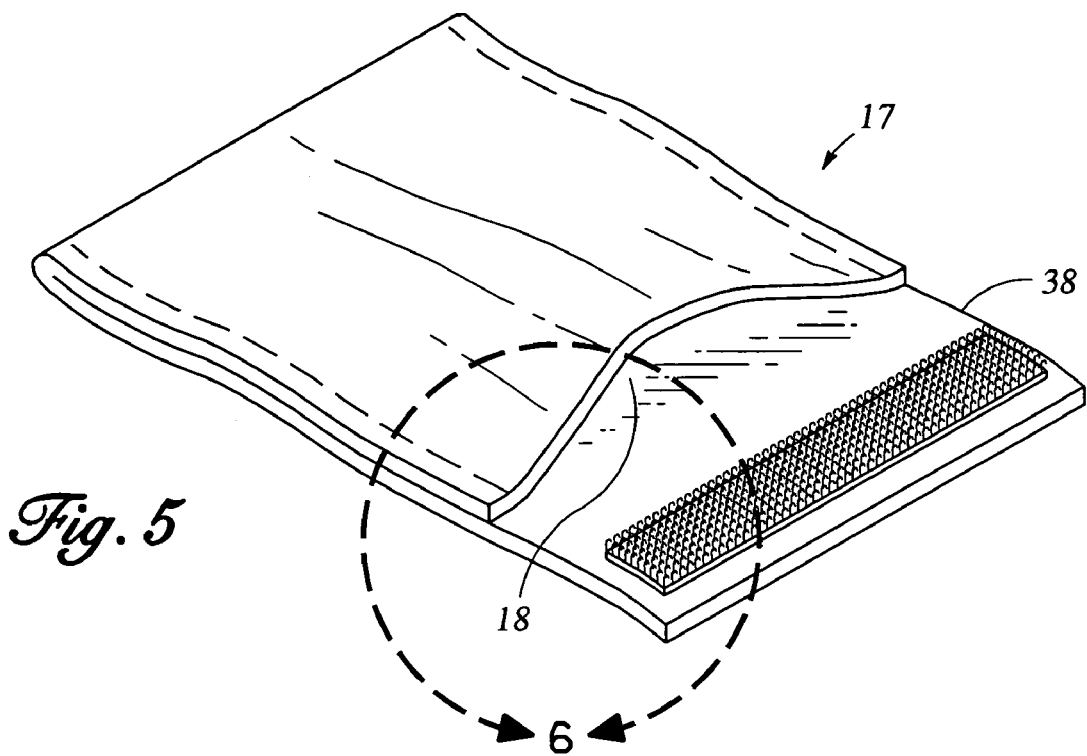
FIG. 5 is a close up view of an ice pocket for use with the overlay of the present invention.

The simple construction of the removable pocket 17 can be seen in FIG. 5. The removable pocket 17 can be made simply by folding a rectangular piece of terrycloth, leaving a flap 38, and sewing the longitudinal sides together, leaving opening 18.

Figure 6:
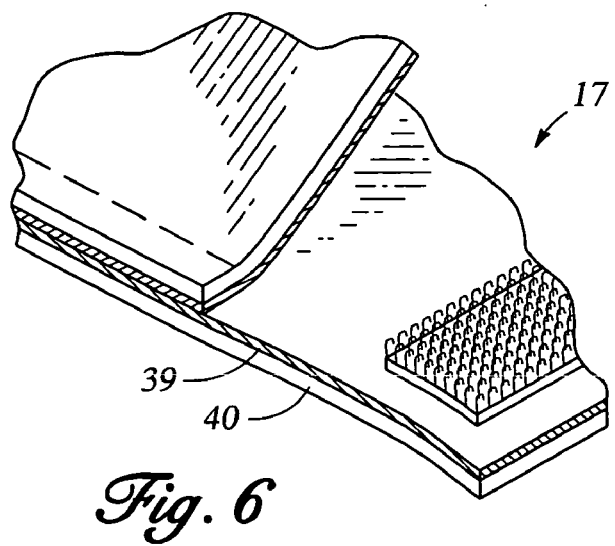
FIG. 6 is a detail view of the layers of the material used in the ice pockets and overlay of the present invention.

Alternatively, as shown in the detail drawing of FIG. 6, for both the removable picket 17 and the overlay 10 itself, a layer 39 of waterproof material or insulating absorbent material can be used with the cotton layer 40 in order to prevent any leakage or condensation from reaching the outside of the overlay 10 and the removable pocket 17.

In yet another embodiment of the invention, the whole overlay 10 can be made of a lightweight plastic material, and adhesive pull tabs, like those on disposable diapers, can be utilized with or in place of the straps and fastening systems. Such an overlay 10 could be disposed of after a single use.

I claim:

1. An overlay for providing cooling therapy to a wearer's shoulder joint and upper arm, the overlay, when laid flat, having an overall configuration in the shape of a block letter capital L, the overlay comprising: a first rectangular segment having an upper end, a lower portion, two sides, a top surface, and a bottom surface, the upper end having two generally parallel spaced-apart straps extending there-from, each of the straps having one part of a two-part fastening system, the straps being configured for being wrapped around the wearer's neck; a second rectangular segment disposed at the lower portion of the first rectangular segment and perpendicular thereto, the second rectangular segment having a top surface, a bottom surface, an upper portion, a lower end, and two sides parallel to the sides of the first rectangular segment, and further having means for removably fastening the sides of the second rectangular segment together around the upper arm of the wearer; a first pocket formed on the top surface of the first rectangular segment, the first pocket having an opening at the lower portion of the first rectangular segment, the opening designed for receiving a removable container of cooling material for placement inside the first pocket; and a second pocket formed on the top surface of the second rectangular segment, the second pocket having an opening at the upper portion of the second rectangular segment, the opening designed for receiving a removable container of cooling material for placement inside the second pocket.

2. The overlay of claim 1 which further comprises a third pocket formed on the top surface of the second rectangular segment next to the second pocket, the third pocket having an opening at the upper portion of the second rectangular segment, the opening designed for receiving a removable container of cooling material for placement inside the third pocket.

3. The overlay of claim 1 wherein the two-part fastening system is selected from the group consisting of a complementary hook and loop fastening system, D-rings, buttons, clasps, a hook and eye combination, and string ties.

4. The overlay of claim 1 which further comprises:
one part of a complementary two-part fastening system attached to the bottom surface of the first rectangular segment along one of the sides;
a fourth pocket with a flap to which is attached a second part of the complementary two-part fastening system, the fourth pocket having an opening designed for receiving a removable container of cooling material for placement inside the fourth pocket.

5. The overlay of claim 1 which further comprises:
one part of a complementary two-part fastening system attached to the bottom surface of the second rectangular segment along the lower end;
a fourth pocket having a second part of the complementary two-part fastening system attached thereto, the fourth pocket having an opening designed for receiving a removable container of cooling material for placement inside the fourth pocket.

6. The overlay of claim 2 which further comprises:
one part of a complementary two-part fastening system attached to the bottom surface of the first rectangular segment along a side;
a fourth pocket having a second part of the complementary two-part fastening system attached thereto, the fourth pocket having an opening designed for receiving a removable container of cooling material for placement inside the fourth pocket;
one part of a complementary two-part fastening system attached to the bottom surface of the second rectangular segment along the lower end;
a fifth pocket having a second part of the complementary two-part fastening system attached thereto, the fifth pocket having an opening designed for receiving a removable container of cooling material for placement inside the fifth pocket.

7. The overlay of claim 1 wherein the containers of cooling material are selected from the group consisting of a zippered plastic bag containing pieces of ice, a preformed ice pack, a cold gel pack, and an "instant" ice pack.

8. The overlay of claim 1 wherein the first rectangular segment and the second rectangular segment are made from soft flexible material.

9. A disposable overlay for providing cooling therapy to a wearer's shoulder joint and upper arm, the overlay, when laid flat, having an overall configuration in the shape of a block letter capital L, the overlay comprising: a first rectangular segment having an upper end, a lower portion, two sides, a top surface, and a bottom surface, the upper end having two generally parallel spaced-apart straps extending therefrom with means for fastening the straps around the wearer's neck; a second rectangular segment disposed at the lower portion of the first rectangular segment and perpendicular thereto, the second rectangular segment having a top surface, a bottom surface, an upper portion, a lower end, and two sides parallel to the sides of the first rectangular segment, and further having means for removably fastening the sides of the second rectangular segment together around the upper arm of the wearer; a first pocket formed on the top surface of the first rectangular segment, the first pocket having an opening at the lower portion of the first rectangular segment, the opening designed for receiving a container of cooling material for placement inside the first pocket; a second pocket formed oh the top surface of the second rectangular segment, the second pocket having an opening at the upper portion of the second rectangular segment, the opening designed for receiving a container of cooling material for placement inside the second pocket; wherein the first rectangular segment, the second rectangular segment, the first pocket, and the second pocket are made from a lightweight plastic material.

10. The disposable overlay of claim 9 wherein the means for fastening the straps around the wearer's neck are adhesive pull tabs, and the means for removably fastening the sides of the second rectangular segment together around the upper arm of the wearer are adhesive pull tabs.

11. The disposable overlay of claim 9 wherein the containers of cooling material are selected from the group consisting of a zippered plastic bag containing pieces of ice, a preformed ice pack, a cold gel pack, and an "instant" ice pack.

* * * * *